United States Patent [19]

Malbrancq et al.

[11] Patent Number: 4,648,866
[45] Date of Patent: Mar. 10, 1987

[54] PROCESS/APPARATUS FOR THE WITHDRAWAL/RETURN OF BODY FLUIDS

[75] Inventors: Jean-Michel Malbrancq, Thiais; Georges Vantard, Villefontaine, both of France

[73] Assignee: Rhone-Poulenc S.A., Courbevoie, France

[21] Appl. No.: 628,845

[22] Filed: Jul. 9, 1984

[30] Foreign Application Priority Data

Jul. 7, 1983 [FR] France .................. 83 11572

[51] Int. Cl.$^4$ ............................................ A61M 37/00
[52] U.S. Cl. ........................................ 604/5; 210/90; 210/195.2; 210/433.2; 604/6
[58] Field of Search ............... 604/5, 6; 210/86, 90, 210/195.2, 258, 427, 433.2

[56] References Cited

U.S. PATENT DOCUMENTS

| Re. 31,688 | 9/1984 | Popovich et al. | 604/6 |
|---|---|---|---|
| 3,811,800 | 5/1974 | Shill | 604/5 |
| 4,086,924 | 5/1978 | Latham, Jr. | 604/6 |
| 4,191,182 | 3/1980 | Popovich et al. | 604/6 |
| 4,350,156 | 9/1982 | Malchesky et al. | 604/6 |

FOREIGN PATENT DOCUMENTS

WO8102979 10/1981 PCT Int'l Appl.

Primary Examiner—C. Fred Rosenbaum
Assistant Examiner—J. Smith
Attorney, Agent, or Firm—Burns, Doane, Swecker & Mathis

[57] ABSTRACT

Process/apparatus for the processing of body fluids, advantageously comprising plasmapheresis technique for the fractionation of whole blood, features (i) means, e.g., a common blood transfusion needle, for withdrawing and returning body fluid from and to a living patient; (ii) a body fluid separating module which comprises an upstream first compartment and a downstram second compartment, and having a semi-permeable membrane body fluid separator disposed therebetween; (iii) first conduit means communicating said withdrawal and return means (i) with the upstream first compartment of said separating module (ii); (iv) means provided along said first conduit (iii) for conveying body fluid in either direction therein; (v) means responsive to said conveying means (iv), adapted to monitor the pressure of body fluid circulating in said first conduit (iii), and provided between said withdrawal and return means (i) and said conveying means (iv); (vi) means for collecting body fluid transported across said semi-permeable membrane and communicating with the downstream second compartment of said separating module (ii); (vii) second conduit means communicating the upstream first compartment of said module (ii) to (viii) means for containing body fluid which has not been transported across said semi-permeable membrane thereof, (ix) third conduit means communicating said container means (viii) to said first conduit means (iii) at a point intermediate said conveying means (iv) and the upstream first compartment of said separating module (ii); (x) means provided along said first conduit (iii) at a point intermediate the upstream first compartment of said separating module (ii) and the juncture of communication between said container means (viii) and the said first conduit means (iii), for conveying body fluid therein in the direction of the said upstream first compartment; and (xi) means for ensuring that the pressure across the said semi-permeable membrane of any body fluid in contact therewith does not exceed predetermined value.

14 Claims, 4 Drawing Figures

PROCESS/APPARATUS FOR THE WITHDRAWAL/RETURN OF BODY FLUIDS

BACKGROUND OF THE INVENTION

1. Field of the Invention

The present invention relates to novel plasmapheresis technique, and, more especially, to novel plasmapheresis process/apparatus for the withdrawal/return of body fluid from/to a patient and requiring but a single needle injection therefor.

2. Description of the Prior Art

Plasmapheresis is a known technique entailing separating the whole blood of a donor into two fractions, the first fraction constituting the plasma phase, while the second fraction constitutes the cellular phase which is typically reinjected back into the donor. The plasma phase is a complex aqueous solution containing protein in particular, while the cellular phase, still containing some of the plasma, comprises the red blood cells (or erythrocytes), the white blood cells (or leucocytes) and the blood platelets.

The technique of plasmapheresis has long been used for animal experimentation. for example, John J. Abel et al, "Plasma Removal with Return of Corpuscles", which appeared in 1914 in *J. Pharmacol. Exp. Ther.*, No. 5, pages 625 to 641, in which dog's blood is centrifuged to effect the separation. Cf. the article by A. Geiger which appeared in 1931 in *J. Phys.*, 71, pages 111–120, entitled "Method of Ultrafiltration in vivo", in which there is described a continuous plasmapheresis procedure on a dog, the separation apparatus used including a membrane-containing separator, the membrane being arranged in a spiral and being selected in such fashion as to enable a plasma solution to be obtained which contained the totality of the proteins in the treated blood, if so desired.

Plasmapheresis has also been used in man for a number of years, as indicated by the article "La plasmapherese - Technique - Indications" by Fr. Oberling et al, *J. Med. Strasbourg*, pp. 227–279 (March, 1968). Plasmapheresis is thus tending to now supercede the total donation of blood since the former technique has the advantage of permitting larger quantities of plasma to be withdrawn from the patient without drawback or disadvantage. Since the elements formed are restored to the donor, the withdrawal sessions can follow each other at shorter time intervals than when blood in its entirety is donated.

Thus, plasmapheresis is a technique of long standing and the subsequent improvements therein concern either centrifugation-based apparatus or membrane-containing apparatus. Among the several improvement patents relating to membrane-containing apparatus, compare Amicon's German Pat. No. 2,100,209 in which is described a container comprising a membrane forming a spiral for the circulation of whole blood withdrawn from a donor and in which pressure is exerted on the blood contained in the container, either by means of a gas, or by means of a syringe plunger subjected to the action of a leaf spring. By comparison with the apparatus of Geiger described above, this apparatus has, on account of its design, the disadvantage of not permitting continuous operation on the patient. U.S. Pat. No. 4,191,182 describes a membrane-containing apparatus and in which the blood continuously withdrawn from the donor is separated into plasma and a cellular fraction which is continuously returned to the donor, this apparatus having as one particular characteristic the ability to allow one portion of the cellular fraction to recirculate in an upstream compartment of the membrane-containing component and the ability to allow the plasma fraction to recirculate in a downstream compartment of the same component. In published International Application No. wo 79/01 121, apparatus is also described which entails permitting the withdrawal of blood from the donor and the reinjection into the donor of the fraction which has not crossed the membrane, in continuous fashion.

However, each apparatus hereinbefore described as allowing continuous plasmapheresis, nonetheless has the particular disadvantage of requiring insertion of a needle into the patient/donor at two different sites, which is obviously rather unpleasant for him.

SUMMARY OF THE INVENTION

Accordingly, a major object of the present invention is the provision of improved plasmapheresis process/apparatus comprising a membrane-containing module which permits, in particular, plasmapheresis procedures to be performed on the donor by injecting a needle at but a single site, using a conventional blood transfusion needle.

Another object of the present invention is improved plasmapheresis process/apparatus permitting, over the course of one session, the blood to be circulated several times from the donor to a blood bag, then from the blood bag to the donor, while the blood passes continuously and in the same direction of circulation in contact with a membrane-containing separatory module.

Another object of this invention is a specially adapted process/apparatus permitting a plasma of very high quality to be obtained under the best filtration yield conditions, while ensuring that there is virtually no haemolysis of the blood.

Another object of the invention is process/apparatus permitting the pressure of the cellular fraction exiting an upstream compartment of the membrane-containing module to be regulated to values generally ranging from 0 to 20 mm of mercury in relative pressure, the downstream compartment being at atmospheric pressure.

Another object of the present invention is process/apparatus permitting about 600 ml of plasma to be withdrawn from a donor in about 45 minutes and even in less time.

Yet another object of the present invention is process/apparatus for withdrawal of plasma in which it is possible to easily adapt the operational strategy to the needs of the donor, the wishes of the operator and the characteristics of the membrane-containing module utilized.

Still another object of the present invention is process/apparatus allowing a session yield to be obtained which is greater than the intrinsic yield of the membrane-containing apparatus. By "session yield" there is intended the ratio of the flow rate of liquid which has crossed the membrane (i.e., the plasma) to the flow rate of blood withdrawn from or restored to the vein of the donor. By "intrinsic yield" of the membrane-containing apparatus there is intended the ratio of the flow rate of filtered plasma to the flow rate of the blood upon entry into the membrane-containing module.

Another object of this invention is process/apparatus permitting the blood to be passed in contact with the membrane at a flow rate which is higher than that of the blood withdrawn from the donor.

Another object of the present invention is process/apparatus in which the volumes of blood in circulation outside the body are small.

And still another object of this invention is process/apparatus equally well adapted to plasmapheresis with restoration to the patient, during the reinjection (or return) phase, of a replacement liquid corresponding in volume to that of the plasma withdrawn.

Briefly, the present invention features process/apparatus permitting body fluid withdrawal from a subject, human or animal, by inserting a needle only once, of a liquid which is brought into contact with the membrane(s) of a module containing semi-permeable membrane(s) during a phase referred to as the withdrawal phase, the said liquid which passes in contact with the membrane being separated into a fraction which is transported across the membrane and a fraction which is not transported across the membrane; and to then cause the fraction of the withdrawn liquid which has not been transported across the membrane to be returned to the subject, during the phase referred to as the return phase, the liquid in contact with the membrane circulating in the same direction over the course of a session which may include several phases of withdrawal and return.

Accordingly, provided hereby is improved plasmapheresis apparatus comprising, with reference to the several Figures of Drawing more fully described hereinbelow:

(i) a device 1 for injection into and withdrawal of body liquid from a subject;

(ii) a module 2 containing a semi-permeable membrane separating this liquid into a fraction which has been transported across the membrane and a fraction which has not been transported across the membrane, said module comprising an upstream compartment 3 and a downstream compartment 4 separated by the membrane 14;

(iii) a conduit 5 operably connecting the withdrawal device 1 to a tubulure 6 communicating with the upstream compartment 3 of the membrane-containing module 2;

(iv) a pump 7 situated along the conduit 5, said pump being capable of rotating (operating) in both directions;

(v) a pressure sensor 13 monitoring the liquid circulating in the conduit 5, said sensor being situated between the withdrawal device 1 and the pump 7, this sensor influencing the speed of rotation of the pump 7 which is controlled thereby;

(vi) a container 20 for collection of the liquid which has been transported across the membrane, this container 20 being in communicating relationship with the outlet of the downstream compartment 4 of the membrane-containing module 2;

(vii) a conduit 16 operably connecting a tubulure 15 in the upstream compartment 3 of the membrane-containing module 2 to a container 17 for collection of the fraction of the liquid which has not been transported across the membrane;

(viii) a conduit 16b operably connecting the container 17 to the conduit 5, the junction between the conduit 16b and the conduit 5 being made at a point A situated between the pump 7 and the tubulure 6 communicating with the upstream compartment 3 of the module 2 containing a semi-permeable membrane;

(ix) a pump 18 situated along the loop defined by the conduit 16, the conduit 16b and the part of the conduit 5 included between junction A and the tubulure 6 communicating with the upstream compartment 3 of the membrane-containing module 2; and (x) means 19 for ensuring that the pressure across the membrane of the liquid circulating in contact with the membrane 14 does not exceed a specified value, said means influencing the speed of rotation of the pump 18 which is under their control.

Also featured hereby is improved process utilizing the aforedescribed apparatus, notably during a plasmapheresis procedure in which a subject donates his plasma.

DETAILED DESCRIPTION OF THE INVENTION

Figure 1:
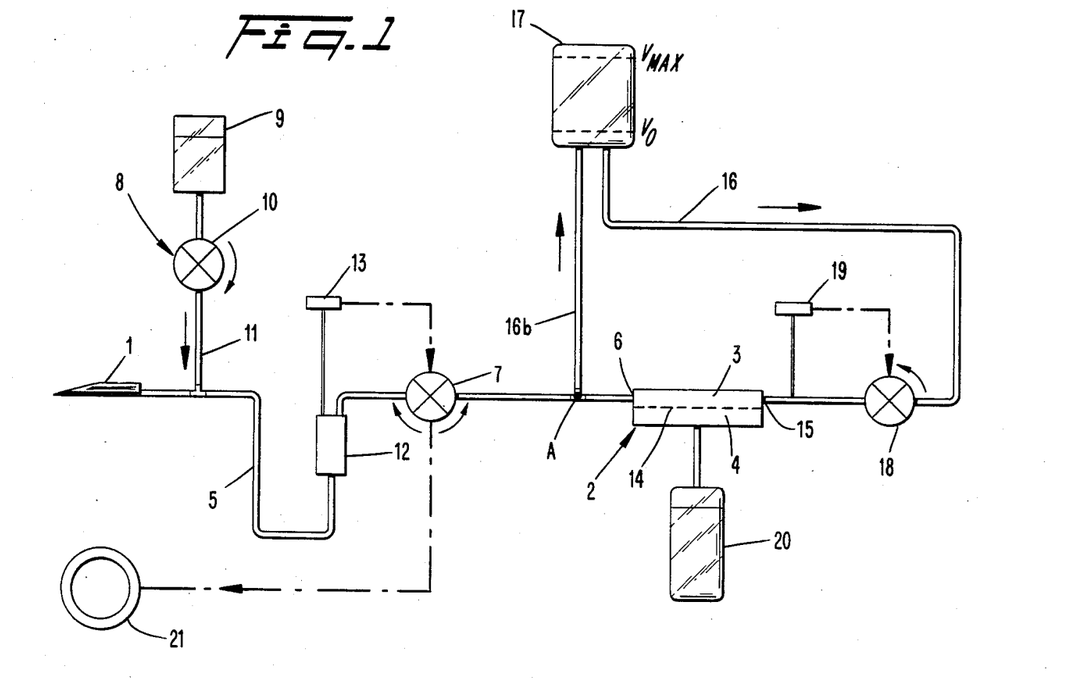
FIG. 1 is a schematic/diagrammatic illustation of one embodiment of the process/apparatus according to the present invention.

More particularly according to the present invention, with reference to the accompanying non-scale Figures of Drawing, in FIG. 1 there is depicted apparatus, especially adapted for donor plasmapheresis, comprising a device 1 for withdrawal of blood from the donor, advantageously a blood sampling needle. As exemplary, the needle can have an external diameter of 1.65 mm and an internal diameter of 1.45 mm, such as those indexed in blood transfusion centers under the designation 16 G. A module 2 containing a semi-permeable membrane 14, and comprising an upstream compartment 3 and a downstream compartment 4, operably communicates with the needle 1 via a conduit 5 extending from said needle 1 to a tubulure 6 which is in communication with the upstream compartment 3 of the membrane-containing module. This conduit 5 typically consists of plastic tubing, made, for example, of polyvinyl chloride. Along this conduit or line 5 is situated a pump 7 which can rotate or operate in both directions, advantageously a peristaltic-type pump. Between the pump 7 and the needle 1 is situated a device 8 adapted to transfer an anticoagulant into the blood flowing from the donor, for example, a glucose solution containing 35.6 g/liter of trisodium citrate, trademark AB 16 of Bieluz Co. This device 8 comprises, for example, a reservoir 9 of anticoagulant, a conduit 11 joined to the conduit 5 and the reservoir 9, and a pump 10, for example a peristaltic pump, situated along the conduit 11. This conduit 11 is joined to the conduit 5 as close as possible to the needle 1. Between the point of junction of the conduits 11 and 5 and the pump 7, a bubble detector 12 and a pressure sensor 13 are advantageously situated in the conduit 5. The tubulure 15 of the upstream compartment 3 of the membrane-containing module 2 is connected by a conduit 16 to a container 17, or bag, for collection of the blood, said container 17 itself being connected via the conduit 16b to the conduit 5, the junction between the conduit 5 and the conduit 16b being made at a point A situated between the pump 7 and the tubulure 6 of the membrane-containing module 2. For clarity in description, this point A will sometimes be referred to as junction A. The conduits 16 and 16b can be made from the same material and be of the same diameters as the conduit 5, while the container 17 advantageously is a bag made from a flexible plastic material. The conduits 16, 16b and the length of the conduit 5 situated between junction A and the tubulure 6 of the membrane-containing module 2 form or define a loop or circulation path for circulation of the fraction of the blood which is not transported across the membrane 14 and which is transferred into the upstream compartment 3 as well as into the container 17. The downstream compartment 4 of the membrane-containing module 2 communicates with a container 20 for collection of the plasma which has been transported across the membrane 14, this container 20 being, for example, a plastic bag.

Along the loop defined above there are, in addition, a pressure sensor 19 and a pump 18 for recirculation of the blood.

In the embodiment of FIG. 1, the pump 18 is situated, within the loop defined above, in the conduit 16 in close proximity to the tubulure 15 of the separation module, while the pressure sensor 19 is situated between the said tubulure 15 and the pump 18.

Figure 2:
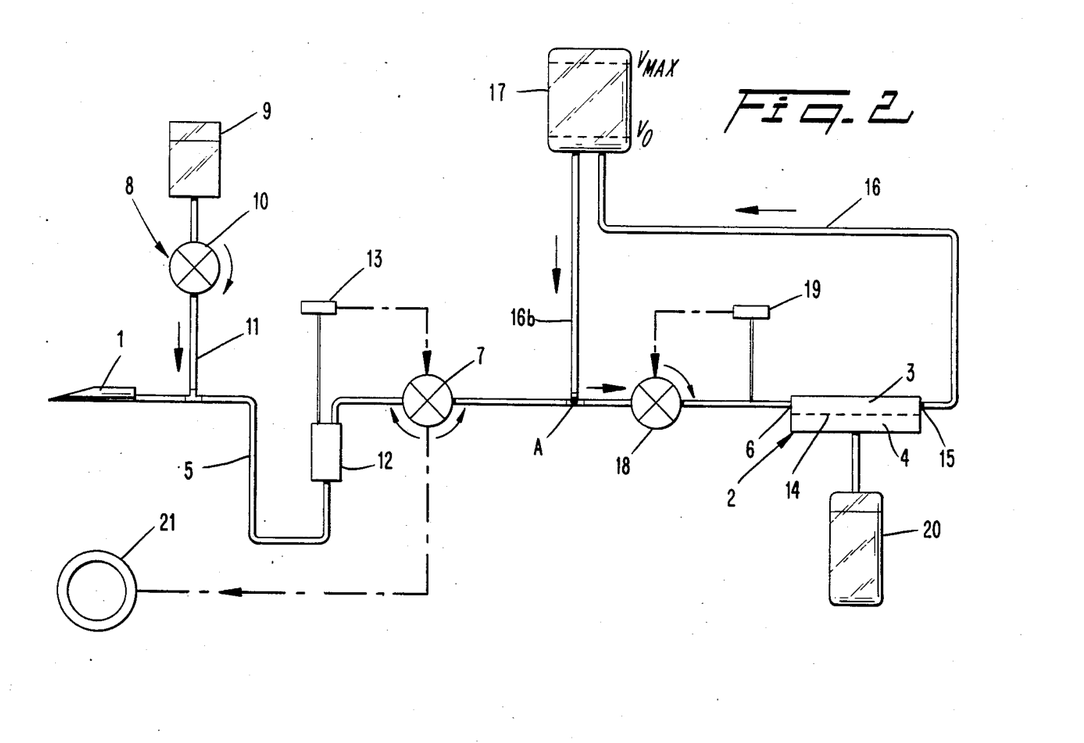
FIGS. 2 and 3 are schematic/diagrammatic illustrations of two other embodiments of process/apparatus according to the present invention.

In the embodiment of FIG. 2, the pump 18 is operably situated, within the loop defined above, between the point of junction A and the tubulure 6 of the membrane-containing module 2, the pressure sensor 19 being positioned between the pump 18 and the said tubulure 6.

Figure 3:
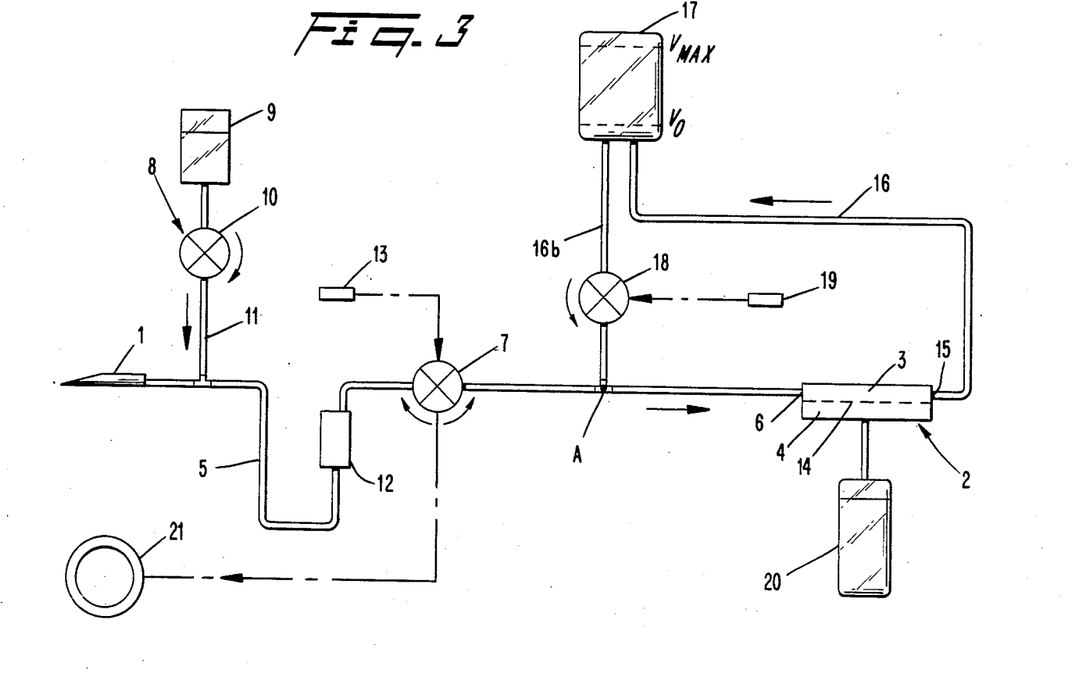

In the embodiment of FIG. 3, the pump 18 is operably situated along the conduit 16b while the pressure sensor 19 is in the conduit 5, between the point of junction A and the tubulure 6 of the membrane-containing module 2.

In the embodiments of FIGS. 1, 2 and 3 described above, the pressure sensor 19 influences the speed of rotation of the pump 18 which is under its control. The arrows placed on the conduits 16b and 16 indicate the direction of recirculation of the blood in the loop during a plasma donation session. The sensor 19 ensures that the blood does not circulate at a pressure greater than a specified selected value, namely, that the pressure across the membrane in the membrane-containing module 2 does not rise above a selected specified value, for example, in order that the blood does not haemolyze.

The embodiments of FIGS. 1 to 4 additionally include a tourniquet 21, known per se, said tourniquet being inflatable and deflatable when desired, by means also per se known, for example, by a compressor, a pressure sensor arresting the inflation of the tourniquet 21 when a specified pressure is attained. The dashed line in FIGS. 1 to 3, between the tourniquet 21 and the pump 7, shows that the inflation or deflation of the tourniquet 21 depends upon the direction of rotation of the pump 7. During the phase of withdrawal of blood from the donor, the tourniquet 21 is inflated, while during the phase of return of blood to the donor which has not been transported across the membrane, the tourniquet 21 is deflated.

The module 2 above described can comprise a membrane in flat or planar form, in spiral form, or in the form of small fine tubes such as hollow fibers. When the membrane comprises a plurality of hollow fibers, the blood advantageously circulates inside the hollow fibers, the combined interior volume of the fibers constituting the upstream compartment 3 of the module.

When the membrane is in flat or spiral form, the blood advantageously circulates between a pair of membranes or series of pairs of membranes, which constitute the upstream compartment 3 of the membrane-containing module 2.

The membranes used for plasmapheresis are preferably those which permit the collection of a plasma: in which all of the proteins of the original blood are found in the same proportions, the protein concentration of which is greater than 55.5 g/liter, in which there are no red cells and in which the concentration of platelets is less than 15,000 platelets per $mm^3$. The membranes selected are those which also permit no haemolysis of blood circulating in contact therewith, while at the same time providing good filtration yields.

These plasmapheresis membranes advantageously have a rejection coefficient for latex of less than 75% for latex particles calibrated at 0.27 microns, and a rejection coefficient for latex of greater than 15% for latex particles calibrated at 0.64 microns. Preferably, the rejection coefficient for latex particles calibrated at 0.27 microns is less than 30%, and the rejection coefficient for latex particles calibrated at 0.64 microns is greater than 90%.

To carry out the aforenoted measurement of latex rejection coefficient, the following procedure is adopted, when the membranes are flat.

50 ml of suspension of calibrated polystyrene particles of diameter 0.27–0.4 or 0.64 microns (marked Rhone-Poulenc under the trademark ESTAPOR) diluted to 0.1% with distilled water, with addition of 1% surfactant (alkylarylsulphonate, trademark SINOZON HAS 60 of the Sinnova Company), are loaded into a cell of type Amicon Model 52.

The Amicon cell is fitted with a sample of the membrane supported on a mesh. An air pressure corresponding to 20 cm of water is established. The first six milliliters of filtrate are recovered for determination of the concentration (cf) of the calibrated particles.

The rejection coefficient is defined by the formula:

$$\frac{(0.1 - cf) \times 100}{0.1}$$

Membranes having the above characteristics are generally of synthetic material, for example, cellulose esters (cellulose nitrate and the like), regenerated cellulose, polycarbonate, and the like. These membranes can also be based on polyether-urethanes containing heparinized ammonium groups, or be of acrylonitrile copolymer. These membranes are advantageously reinforced by a mesh when they are in the form of flat membranes and advantageously have a thickness of between 50 and 200 microns.

Figure 4:
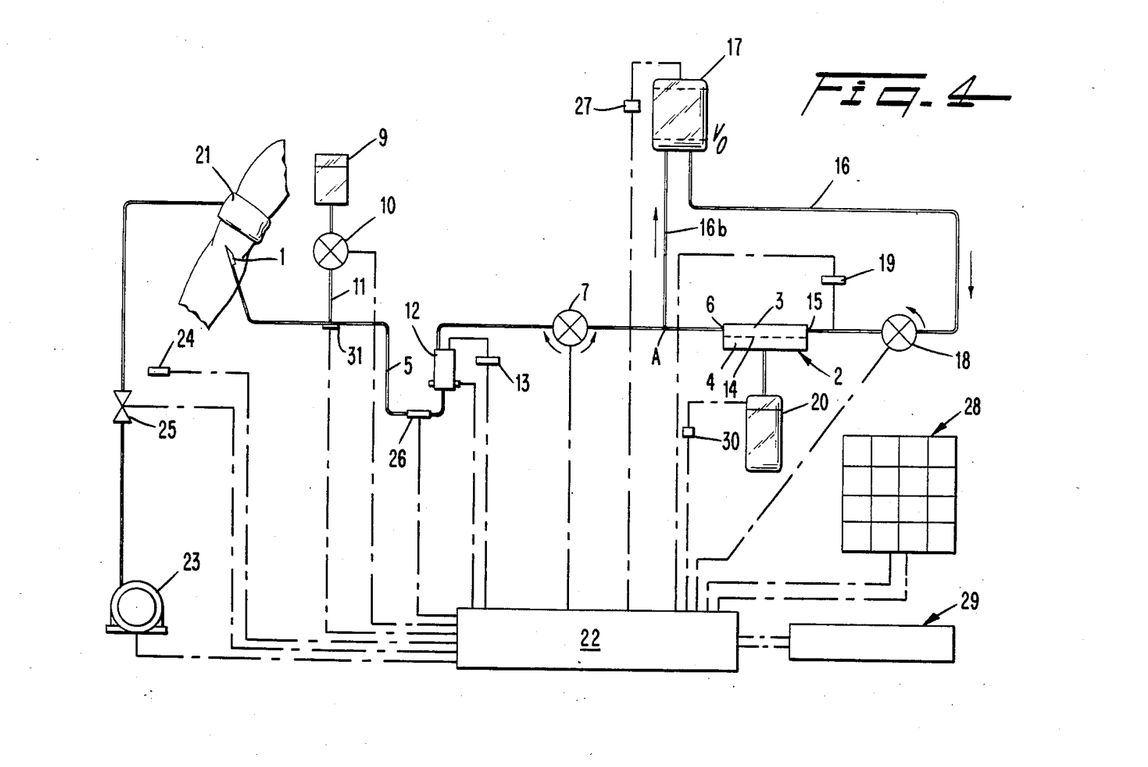
FIG. 4 is another representation of the process/apparatus of FIG. 1 in which, in particular, have been added the connections to a device for monitoring and control.

FIG. 4 represents an embodiment equivalent to that of FIG. 1, but in which are shown the electrical connections of the different components to a logic unit 22 for control and monitoring, the electrical leads being represented by dashed lines. The unit 22 is connected to a current source (not shown). Naturally, all of the elements of the subject apparatus can be consolidated on a console or desk having castors, for example, to facilitate shifting. The description of the logic unit 22 and also of the keyboard 28 and display unit 29, referred to hereinbelow, is not described here in great detail, since the creation of the electronic circuits and advantageous utilization of microprocessors and memories would be trivially apparent to the technician once the problem in question has been considered, i.e., after the technician has been requested to arrange that the apparatus described should function automatically and reliably. The embodiments of FIGS. 2 and 3 are advantageously, and in the same manner, connected to a logic unit 22 for control and monitoring (not shown).

The apparatus of FIGS. 1 to 4 is used as, for example, in the case of a donor plasmapheresis procedure. The conduit 11 is first filled with the citrate solution, and since the junction between the conduit 11 and the conduit 5 is in point of fact very close to the needle 1, the latter may be considered to be at least in part filled with this citrate solution. The tourniquet 21 having been previously inflated to the desired pressure (about 60 mm of mercury) by means of the compressor 23 in conjunction with the electromagnetic valve 25 and contact manometer 24, the needle 1 is inserted into a vein of the donor after conventional prepraration of the insertion site, which is situated between the tourniquet and the extremity of the selected limb. At this moment the pump 10 introduces citrate into the conduit 5, while the pump 7 rotates in the direction which causes the blood to flow towards the tubulure 6 of the membrane-containing module 2 and into the container 17 through the conduit 16b. The pump 7 is under the control of the pressure sensor 13 such that the pressure measured at this point in the conduit 5 always remains greater than a certain value, generally, close to 0 mm of mercury, designated the threshold pressure, to ensure that the pump 7 does not draw the blood directly from the donor's vein. If the pressure in this part of the line becomes lower than the specified pressure fixed at the sensor 13, the logic unit 22 automatically operates and temporarily arrests or slows down the rotation of the pump 7, as long as the required pressure has not returned. When the blood in the container 17 reaches a minimum volume Vo, the pump 18 is activated and causes the blood to circulate in contact with the membrane 14 in the upstream compartment 3 of the module 2, the blood following the course indicated by the arrows in the loop containing the conduits 16b and 16. The pump 18 associated with the pressure sensor 19 is placed in the loop 16, 16b such as to be upstream of the membrane-containing module 2. The sensor 19 indicates the pressure of the blood at entry into the membrane-containing module 2. The determination of the volume Vo may be made by a tachymetric device functioning in association with the pump 7. The pump 18 can for a very short period of time (for example, 15 seconds) rotate at the same speed as the pump 7, then its speed of rotation subsequently increases such that the speed of circulation of the blood in the loop shall be greater than that of the blood in the conduit 5 outside of the loop. The speed of circulation of the blood in the loop can be, for example, 1.5 to 7 times greater than that of the blood withdrawn from the donor. The pressure sensor 19 ensures that the pressure across the membrane in the membrane-containing module 2 does not exceed a predetermined specified value, in order not to haemolyze the blood. The pressure sensor 19 is adjusted such that the blood penetrates into the upstream compartment 3 of the membrane-containing module 2 at a pressure generally ranging from 40 to 100 mm of mercury in relative terms, and preferably from 50 to 90 mm of mercury, when the plasma is at atmospheric pressure in the downstream compartment 4 of the membrane-containing module 2. If this maximal desired value is exceeded, the logic unit 22 automatically arrests or slows down the pump 18.

The period during which the blood leaves the vein of the donor is called the withdrawal phase. The latter comes to an end, for example, according to the predetermined volume of blood desired to be withdrawn from the donor (in each withdrawal phase), this volume naturally always being less than the volume of the container 17 for collection of the blood circulating in the loop. Advantageously, a tachymetric device is operably associated with the pump 7 and when the desired volume of blood is withdrawn from the donor, the logic unit 22 operates and arrests the pumps 7 and 10. During this withdrawal phase the blood circulating in the loop tends to undergo an increase in its haematocrit; the sensor 19 will operate to slow the speed of the pump 18 when the pressure increases. The logic unit 22 actuates the electromagnetic valve 25, which becomes set such that the tourniquet 21 deflates, and also the pump 7, setting it in motion in the opposite direction to that in the preceding phase, referred to as the withdrawal phase. Thus begins the phase referred to as the return phase, during which the blood contained in the bag 17 returns to the donor while circulating in part in the loop (16, 16b) and passing in contact with the membrane 14 of the module 2. During this return phase, as previously during the withdrawal phase, the blood circulating in the loop tends to undergo an increase in its haematocrit, since more plasma passes into the container 20. The sensor 19 will operate in this case to slow the speed of rotation of the pump 18 when the pressure rises. It is, indeed, possible to arrange that, from the beginning of the return phase, the speed of rotation of the pump 18 should be slowed slightly, while causing it to circulate the blood in the loop at a speed greater than that of the blood returning to the donor. During the return phase, during which the pump 10 supplying citrate is not operating, the blood passes into the bubble detector 12. If any bubbles are detected by the detector 12, the logic unit 22 immediately arrests the pump 7 and, if necessary, actuates a clamp 26, or similar obstruction device, which closes the conduit 5. During the return phase, the pressure sensor 13 acts as a safety device, in the sense that it is adjusted in such manner that the pressure of the blood does not exceed a certain predetermined value. If this value is exceeded, for example, through total or partial obstruction of the needle 1, the logic unit 22 intervenes immediately to arrest or slow the pump 7. During the return phase, the blood can, if necessary, pass through a conventional filter provided in the bubble detector, to avoid the possibility of returning undesirable particles to the donor. This filter can, for example, be moved aside during the withdrawal phase, returning to a seating provided in the bubble detector during the return phase. During the return phase, the pump 18 rotates, or operates in the same direction as during the withdrawal phase, the blood thus circulating in the loop (16, 16b) in the direction of the arrows during the phases of withdrawal and return. The completion of the return phase is detected, for example, by a balance-containing device 27 connected to the logic unit 22, the said balance enabling the return phase to be concluded when the volume Vo is reached in the container 17. The logic unit 22 then causes the apparatus to again operate in the withdrawal phase, i.e., the tourniquet 21 is inflated after the compressor 23 has started and the valve 25 has been set in the appropriate position; and starts the pump 7 in motion in the opposite direction, such that the blood of the donor is conveyed from the needle 1 towards the container 17 in the loop, which comprises in particular the conduits 16 and 16b and also the upstream compartment 3 of the membrane-containing module 2. The pump 10 which distributes the anticoagulant is also set in motion from the beginning of the withdrawal phase. When, during the last return phase, it is seen that the container 20 for collection of plasma is sufficiently full, the procedure is stopped completely, after having emptied the container 17 and the conduit 5 at least as far as the bubble detector 12, during the last return phase.

The flow rate of the pump 10 is generally adjusted such that, during the phase referred to as the withdrawal phase, one volume of citrate is used for 8 volumes of blood, or preferably 1 volume of citrate for 16 volumes of blood, the ratio being selected by the apparatus operator. This dilution ratio is advantageously obtained by placing the speed of rotation of the pump 10 under the control of that of the pump 7.

It will, thus, clearly be seen that the apparatus according to the present invention can be made the subject of highly elaborate automation. Thus, as is shown more especially in FIG. 4, the logic unit 22 for control and monitoring can be connected to a keyboard 28 and a display unit 29. Likewise, the logic unit 22 can be connected to a synoptic chart (not shown) on which the localization of any anomalous functioning is indicated to the operator by a warning light, at the same time that, for example, an audible signal is emitted. On the keyboard 28 it is possible to choose the maximum volume of blood desired to be circulated during the withdrawal phase (300, 350, 400, 450 cm$^3$ of blood, for example), by pressing the corresponding key. It is also possible to choose the volume of plasma desired to be withdrawn during the session (400, 500 or 600 cm$^3$, for example), by pressing the corresponding key. Thus, a device 30 is advantageously provided on the plasma bag 20 to enable the quantity of plasma withdrawal to be known instantaneously as the session progresses, this device 30, known per se, being connected to the logic unit 22. On the keyboard 28, a key can also be provided for automatic priming of the line 11 before inserting the needle into the donor. By pressing this key, the pump 10 starts and stops automatically when the solution of citrate is detected, for example, at the junction 31 of the two lines 11 and 5. On the keyboard 28, it is also possible to provide, for example, a key to show on the display unit 29 the instantaneous volume of plasma in the bag 20 at any moment, a key to show on the display unit 29 the flow rate of the blood from the pump 7, to show the timing of the session in progress, and the like. The apparatus can include, in conjunction with the logic unit 22 and the values designated at the keyboard 28 regarding the volume of blood desired during the withdrawal phase and the total volume of plasma desired, an integration system operating during the last withdrawal phase such that the volume of blood withdrawn enables the total desired volume of plasma to be obtained upon completion of the last return phase.

Numerous variations of the apparatus described above will be apparent to one skilled in this art. By way of example, the apparatus can include a small collapsible balloon in the line 5 between the junction 31 and the clamp 26. This small balloon then serves as a double security device with the pressure sensor 13, in the sense that it closes when the flow rate at the pump 7 is greater than that from the vein, if the sensor has not functioned during the withdrawal phase. This small collapsible balloon can, if necessary, be substituted for the sensor 13.

Likewise, the device 8 intended for introducing the anticoagulant can optionally be omitted, if the interior of the needle 1, bubble detector 12 and lines 5, 16 and 16b is coated, for example, with a polymer based on polyether-urethanes containing heparinized ammonium groups, such as those described in particular in U.S. Pat. No. 4,046,725. If necessary, the lines 5 and 16 can comprise a polymer such as those described in the aforesaid '725 patent, or a mixture of polyvinyl chloride and polyether-urethane containing heparinized ammonium groups, such as the mixtures noted in published European Patent Appliation No. 12,701. The microporous membrane can also be prepared from a mixture of polymers according to said published European Patent Application No. 12,701. Likewise, the subject apparatus can include a detector, known per se, in the line 11 enabling the absence of anticoagulant in the reservoir 9 to be indicated. Likewise, the apparatus too can include an optical detector in the line connecting the container 20 to the membrane-containing module 2, enabling the presence of haemoglobin in the filtered plasma to be indicated.

The embodiments of FIGS. 2 and 3 comprise the same constituent components as those according to FIGS. 1 or 2, however, with the difference that the pump 18 and the pressure sensor 19 are positioned in a different manner in the loop comprising the conduits 16 and 16b. In the case of the embodiment of FIG. 2, the pump 18 is situated in the portion of the conduit 5 between the point of junction A and the tubulure 6 of the upstream compartment 3 of the module 2, the sensor 19 being positioned between the pump 18 and the said tubulure 6. In the embodiment of FIG. 3, the pump 18 is situated in the conduit 16b, while the sensor 19 is situated close to the tubulure 6 of the upstream compartment 3 of the module 2, in the portion of the conduit 5 between the point of junction A and the tubulure 6. In the embodiments of FIGS. 2 and 3, the direction of rotation of the pump 18 is such that the latter and the sensor 19 associated with it are situated, as in the embodiment of FIG. 1, upstream of the membrane-containing module 2.

To use the apparatus illustrated in FIG. 2, once the first phase of withdrawal from the donor has begun, the pump 18 can be rotated at the same speed as the pump 7, as long as the volume Vo is not reached in the container 17, and then the speed of rotation of the pump 18 is accelerated. During the plasmapheresis session, the blood circulates in the direction of the arrows in the loop, i.e., passing from the upstream compartment 3 of the module 2 into the conduit 16, then into the container 17 and the conduit 16b, and returns via the tubulure 6 into the upstream compartment 3 of the module 2.

To use the apparatus illustrated in FIG. 3, once the first phase of withdrawal from the donor has begun, it is possible to commence by rotating the pump 18 such that it draws into the container 17 one fraction of the blood withdrawn, while the other fraction of the blood withdrawn passes into the upstream compartment 3 of the membrane-containing module 2, entering via the tubulure 6, and then into the container 17. When the volume Vo is reached in the container 17, the direction of rotation of the pump 18 is then reversed, and the pump is set to rotate at a speed which allows a greater speed of circulation of the blood in the loop than the speed of circulation of the blood withdrawn from the donor.

During the session, within the loop, the blood circulates following the same direction of circulation as that according to the embodiment of FIG. 2, i.e., it passes from the upstream compartment 3 of the membrane-containing module 2 into the conduit 16, then into the container 17, and into the conduit 16b to return via the tubulure 6 of the upstream compartment 3 of the membrane-containing module 2.

With the apparatus such as depicted in FIGS. 1 and 4, and described above, plasmapheresis procedures have been performed on a donor using, by way of example, a membrane-containing module 2 in which the total membrane area is 600 cm$^2$ and which contains two membranes arranged facing each other forming the upstream compartment 3 between which the blood circulates. Each membrane is 30 cm long and 10 cm wide and supported on a mesh, as described in more detail below. The average thickness of the blood film is 500 microns. The withdrawal device 1 is a needle of 1.65 mm external diameter and 1.45 mm internal diameter. The conduits 5, 16 and 16b are made from polyvinyl chloride (PVC) and have an internal diameter of 3.5 mm. The conduit 11 is also made of PVC and has an internal diameter of 0.9 mm. The pump 10 is a peristaltic pump (reference RP 04, marketed by Hospal), said pump comprising a silicone envelope.

The pumps 7 and 8 are peristaltic pumps (reference RP 01, also marketed by Hospal), said pumps also comprising a silicone envelope. The containers 17 and 18 have a capacity of 1,000 cm$^3$ and are also made of PVC.

The membrane used is a membrane supported on a mesh, obtained from a solution of polymer in an organic solvent which is permitted to flow onto a mesh rotating in contact with a belt having a very smooth surface. This solution contains 8% by weight of a copolymer of acrylonitrile/methyl methacrylate/sodium methallyl sulfonate, comprising 7.75% by weight of methyl methacrylate and 80 mEq/kg of acidic residue, dissolved in a mixture of N-methylpyrrolidone/glycerin (70.8/21.2%). This copolymer has a specific viscosity of 0.3 at 20° C. in solution at a concentration of 2 g/liter in dimethylformamide.

The mesh used is a monofilament fabric of ethylene glycol polyterephthalate, having a mesh size of 75 microns, the thread diameters being 55 microns and the open or voids area being 33%. This mesh weighs 55 g/m$^2$.

The microporous membrane which is obtained, supported on the mesh, has a thickness of 120 microns and its mass is 10 g of polymer per m$^2$ of dry membrane.

The microstructure of the polymer phase of the membrane is porous and regular. Its porosity is 80%, the porosity being defined as the ratio (multiplied by 100) of the volume of the pores to the total volume of the membrane (polymer+pores).

The flow rate for water (with 1% of a surfactant added) of this membrane supported on the mesh is 4.5 ml/h cm$^2$ mm Hg.

The rejection coefficient for latex of this membrane is:
(i) 5 to 15% for latex calibrated at 0.27 microns
(ii) 65 to 80% for latex calibrated at 0.4 microns
(iii) 98 to 100% for latex calibrated at 0.64 microns The sensor 13 is a sensor from National Semiconductor, trademark Lx 1 801 GB, in which the minimal pressure registered is adjusted to 10 mm of mercury during the withdrawal phase and the maximal pressure value is adjusted to 80 mm of mercury (in relative value) during the return phase. The sensor 19 is a sensor of the same make and same reference as the sensor 13. The sensor 19 is adjusted to a maximal relative pressure of 60 mm of mercury. The containers 17 for collection of the blood and 20 for collection of the plasma are at atmospheric pressure and are placed without alteration of level in relation to the membrane-containing module 2. Given that the pressure of the blood upon leaving the upstream compartment 3 is 10 mm of mercury, due to the loss of pressure head in the line 16b, the average pressure across the membrane is equal to:

$$\frac{60 + 10}{2} = 35 \text{ mm of mercury}$$

During each withdrawal phase, the tourniquet is inflated to 60 mm of mercury and the flow rate of citrated blood is 60 ml/mm in the line 5, between the needle 1 and the pump 7. The speed of recirculation of the blood in the loop (16, 16b) is 170 ml/mm during each withdrawal phase.

With the apparatus as defined above, fixing the volume of blood at 450 cm$^3$ during the withdrawal phase, the total volume of plasma to be collected at 600 cm$^3$, and the ratio of the volume of coagulant solution/volume of blood at 1/16, during each withdrawal phase, the plasmapheresis procedure was completed in 50 minutes after having performed 5 withdrawal phases and 5 return phases.

The plasma collected is practically acellular. It contains no contamination by red cells and only 3,000 platelets per mm$^3$. The protein concentration of the plasma is 57 g/liter. The apparatus according to the invention has thus enabled a session yield of 20% to be obtained with a membrane-containing module, the intrinsic yield of which is only 11.5%.

By way of comparison, 87 minutes was needed to collect 600 ml of plasma in a plasmapheresis procedure performed under the same conditions of blood flow in the line 5, i.e., 60 ml/mm, and pressure across the membrane with the same membrane-containing module 2, but without recirculation of the blood, i.e., eliminating the line 16b and adding a pressure sensor between the pump 7 and the membrane-containing module (in the embodiments shown in FIGS. 1 and 4).

The apparatus as above described can very obviously be used with animals (dogs, horses, etc.), in particular for plasmapheresis procedures.

Generally, the subject apparatus can be used every time it is desired to insert a needle into a subject (human or animal) at only one single site, using a simple needle (having only one internal channel), and to cause the withdrawn liquid (generally blood) to pass in contact with a semipermeable membrane at a speed of circulation greater than that of the liquid withdrawn, the liquid which has not been transported across the membrane returning to the subject by the same conduit which was used for the withdrawal.

Thus, the apparatus described above can be used for applications other than donor plasmapheresis. According to the separation characteristics of the semipermeable membranes used, it will be possible to deplete the circulating blood of only certain of its proteins or certain constituent components of the plasma. It is also possible to perform haemofiltration sessions by means of, for example, the reinjection of a replacement liquid determined by the quantity of filtered liquid collected in the container 20.

The subject apparatus can also be used for plasma exchange procedures, i.e., reinjecting into the patient, during the return phase, a plasma equivalent in quantity to that withdrawn, by means of a pump and conduit (not shown) attached, for example, to the conduit 5 between the bubble detector 12 and the pump 7. If the patient has an arterio-venous shunt, it is not necessary to use the tourniquet 21.

The apparatus according to this invention can also be used for the treatment of the ascites fluid of a patient, there being no need in this application for the tourniquet, the device 8 for introduction of the anticoagulant, or the bubble detector 12.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. Apparatus for processing of body fluids, comprising (i) means for withdrawing and returning body fluid from and to a living patient; (ii) a body fluid separating module which comprises a first compartment, a second compartment and a semi-permeable membrane disposed between said first and second compartments, said semi-permeable membrane being permeable to a liquid fraction of the body fluid, said second compartment being adapted to receive liquid fraction which permeates through said semi-permeable membrane from said first compartment; (iii) first passage means communicating said withdrawal and return means (i) with the upstream first compartment of said separating module (ii); (iv) first pumping means provided at a location along said first passage means (iii) for pumping body fluid in either direction through said first passage means; (v) first sensor means controlling said first pumping means (iv), said first sensor means adapted to monitor pressure of body fluid passing through said first passage means (iii), said first sensor means operatively provided between said withdrawal and return means (i) and said first pumping means (iv); (vi) means for collecting from the second compartment the liquid fraction received by the second compartment; (vii) second passage means communicating an end of the first compartment (viii) with container means, (ix) third passage means communicating said container means (viii) with another end of said first compartment so that said second and third passage means and said first compartment define a circulation path, said first passage means communicated with said circulation path at a juncture with said third passage means; (x) second pumping means on said circulation path for pumping body fluid through said circulation path, whereby a pressure may be maintained in said first upstream compartment greater than that in said second downstream compartment; and (xi) means for controlling said second pumping means so that the pressure difference across said semi-permeable membrane does not exceed a predetermined value.

2. The apparatus as defined in claim 1, further comprising an inflatable tourniquet, inflating means adapted to inflate said tourniquet upon withdrawal of body fluid from the patient, and deflating means adapted to deflate said tourniquet upon the return of body fluid to the patient.

3. The apparatus as defined in claim 1, further comprising means for monitoring the volume of body fluid in said container means, and means for reversing said first pumping means (iv) when the body fluid in said containing means (viii) equals a predetermined volume.

4. The apparatus as defined in claim 3, wherein said container monitoring means also monitors completion of a phase of return of body fluid to the patient.

5. The apparatus as defined in claim 1, further comprising means for monitoring the amount of liquid fraction collected in said collection means (vi).

6. The apparatus as defined in claim 1, further comprising a body fluid bubble trap at a location along said first passage means (iii) between said first pump means (iv) and said withdrawing and returning means.

7. The apparatus as defined in claim 1, further comprising means for introducing an anticoagulant in to the body fluid during a phase of withdrawal of body fluid from said patient.

8. The apparatus as defined in claim 1, further comprising logic circuitry for the automatic control and monitoring of said apparatus.

9. A plasmapheresis process comprising operating a first pump to withdraw body fluid from a living patient through a first passage, operating a second pump to continuously circulate withdrawn body fluid along a circulation path connected to said first passage and passing by a semi-permeable membrane, whereby a fraction of said circulating body fluid permeates through said semi-permeable membrane and is collected and when the recirculating blood equals a predetermined maximum quantity, operating said first pump in reverse to return to the patient the recirculating body fluid through said first passage.

10. The process as defined in claim 9, further comprising the step of repeating the steps of the process until a preselected quantity of the fraction is collected.

11. A plasmapheresis process comprising the steps of:
inflating a tourniquet on a living patient and operating a first pump in a first direction to withdraw blood at a first speed from the living patient through a first passage, said first passage provided with a device for dispensing anticoagulant and a bubble trap, said blood being withdrawn to a first container;

upon said first container receiving a predetermined minimum quantity, operating a second pump to circulate blood at a second speed greater than said first speed along a circulation path from said first container through a first compartment of a separating module and back to said first container, said circulation path including second and third passages each communicating said first container with said first compartment, said first passage communicating with one of said second and third passages, said circulating step including passing the blood along a membrane of said first compartment so that a plasma fraction of the blood permeates through the membrane and controlling the second pump with a pressure sensor to prevent pressure difference across the membrane from exceeding a predetermined value;

collecting in a second container the plasma fraction which permeates through said membrane;

when a predetermined maximum quantity of blood is withdrawn to said first container, performing a return phase comprising the steps of deflating said tourniquet and operating said first pump in a reverse direction to return blood from the first container to the living patient through the first passage while maintaining operation of said second pump; terminating said return phase when the blood in said first chamber equals said predetermined miminum quantity.

12. The process of claim 11, further comprising the step of repeating the process until a preselected quantity of plasma is collected in the second container.

13. The process as defined by claim 9, wherein said body fluid comprises human blood.

14. The process as defined by claim 9, wherein the speed of circulation of body fluid exceeds the speed of withdrawal of body fluid through the first passage.

* * * * *